United States Patent
McClellan (10) Patent No.: US 9,827,140 B2
(45) Date of Patent: Nov. 28, 2017

(54) PERCUTANEOUS BLEPHAROPLASTY DEVICE AND METHOD

(71) Applicant: William Thomas McClellan, Morgantown, WV (US)

(72) Inventor: William Thomas McClellan, Morgantown, WV (US)

(*) Notice: Subject to any disclaimer, the term of this patent is extended or adjusted under 35 U.S.C. 154(b) by 452 days.

(21) Appl. No.: 14/333,910

(22) Filed: Jul. 17, 2014

(65) Prior Publication Data

US 2015/0025604 A1 Jan. 22, 2015

Related U.S. Application Data

(60) Provisional application No. 61/847,218, filed on Jul. 17, 2013.

(51) Int. Cl.
| | | |
|---|---|---|
| *A61B 18/12* | (2006.01) | |
| *A61F 9/007* | (2006.01) | |
| *A61B 18/00* | (2006.01) | |
| *A61B 18/14* | (2006.01) | |

(52) U.S. Cl.
CPC .......... *A61F 9/00718* (2013.01); *A61B 18/12* (2013.01); *A61B 18/1485* (2013.01); *A61B 2018/0047* (2013.01); *A61B 2018/00916* (2013.01); *A61B 2018/1425* (2013.01); *A61B 2018/1467* (2013.01)

(58) Field of Classification Search
CPC .............. A61F 9/00718; A61N 1/0452; A61B 2017/00973; A61B 2018/1425; A61B 2018/1467; A61B 2018/1475; A61B 18/14

See application file for complete search history.

(56) References Cited

U.S. PATENT DOCUMENTS

| | | |
|---|---|---|
| 2,032,860 A | 3/1936 | Wappler et al. |
| 2,056,377 A | 10/1936 | Wappler |
| 3,828,780 A | 8/1974 | Morrison, Jr. |
| 3,901,242 A | 8/1975 | Storz |
| 3,920,021 A | 11/1975 | Hilterbrandt |
| 3,920,022 A * | 11/1975 | Pastor ................ A61B 18/1402 606/41 |
| 3,939,839 A | 2/1976 | Curtiss |
| 3,970,088 A | 7/1976 | Morrison |
| 4,043,342 A | 8/1977 | Morrison, Jr. |
| 4,074,718 A | 2/1978 | Morrison, Jr. |
| 4,116,198 A | 9/1978 | Roos |
| 4,181,131 A | 1/1980 | Ogiu |
| 4,202,337 A | 5/1980 | Hren et al. |
| 4,228,800 A | 10/1980 | Degler, Jr. et al. |
| 4,232,676 A | 11/1980 | Herezog |
| 4,326,529 A | 4/1982 | Doss et al. |
| 4,381,007 A | 4/1983 | Doss |
| 4,476,862 A | 10/1984 | Pao |
| 4,517,975 A | 5/1985 | Garito et al. |

(Continued)

*Primary Examiner* — Daniel Fowler
(74) *Attorney, Agent, or Firm* — Andrew D. Wright; Roberts Mlotkowski Safran Cole & Calderon, P.C.

(57) ABSTRACT

Approaches for percutaneous blepharoplasty are provided. An electrosurgical device includes: a hand-piece; a tip connected to the hand-piece; and two needles extending from a distal end of the tip. The hand-piece is structured and arranged to connect to an electrical energy source, and to convey electrical energy from the electrical energy source to the needles in a percutaneous blepharoplasty procedure.

2 Claims, 7 Drawing Sheets

(56) References Cited

U.S. PATENT DOCUMENTS

| | | |
|---|---|---|
| 4,532,924 A | 8/1985 | Auth et al. |
| 4,548,207 A | 10/1985 | Reimels |
| 4,567,890 A | 2/1986 | Ohta et al. |
| 4,593,691 A | 6/1986 | Lindstrom et al. |
| 4,674,499 A | 6/1987 | Pao |
| 4,682,596 A | 7/1987 | Bales et al. |
| 4,706,667 A | 11/1987 | Roos |
| 4,765,331 A | 8/1988 | Petruzzi et al. |
| 4,805,616 A | 2/1989 | Pao |
| 4,823,791 A | 4/1989 | D'Amelio et al. |
| 4,920,978 A | 5/1990 | Colvin |
| 4,931,047 A | 6/1990 | Broadwin et al. |
| 4,936,281 A | 6/1990 | Stasz |
| 4,943,290 A | 7/1990 | Rexroth et al. |
| 4,966,597 A | 10/1990 | Cosman |
| 4,976,711 A | 12/1990 | Parins et al. |
| 4,998,933 A | 3/1991 | Eggers et al. |
| 5,007,908 A | 4/1991 | Rydell |
| 5,009,656 A | 4/1991 | Reimels |
| 5,047,026 A | 9/1991 | Rydell |
| 5,047,027 A | 9/1991 | Rydell |
| 5,078,717 A | 1/1992 | Parins et al. |
| 5,080,660 A | 1/1992 | Buelna |
| 5,084,044 A | 1/1992 | Quint |
| 5,085,659 A | 2/1992 | Rydell |
| 5,088,997 A | 2/1992 | Delahuerga et al. |
| 5,098,431 A | 3/1992 | Rydell |
| 5,112,330 A | 5/1992 | Nishigaki et al. |
| 5,122,138 A | 6/1992 | Manwaring |
| 5,125,928 A | 6/1992 | Parins et al. |
| 5,143,063 A | 9/1992 | Fellner |
| 5,167,659 A | 12/1992 | Ohtomo et al. |
| 5,171,311 A | 12/1992 | Rydell et al. |
| 5,178,620 A | 1/1993 | Eggers et al. |
| 5,192,280 A | 3/1993 | Parins |
| 5,195,959 A | 3/1993 | Smith |
| 5,196,007 A | 3/1993 | Ellman et al. |
| 5,197,466 A | 3/1993 | Marchosky et al. |
| 5,197,963 A | 3/1993 | Parins |
| 5,207,675 A | 5/1993 | Canady |
| 5,217,457 A | 6/1993 | Delahuerga et al. |
| 5,217,459 A | 6/1993 | Kamerling |
| 5,226,904 A | 7/1993 | Gentelia et al. |
| 5,267,994 A | 12/1993 | Gentelia et al. |
| 5,267,997 A | 12/1993 | Farin et al. |
| 5,273,524 A | 12/1993 | Fox et al. |
| 5,346,489 A * | 9/1994 | Levy .................... A61B 18/201 606/15 |
| 5,354,296 A | 10/1994 | Turkel |
| 5,395,369 A | 3/1995 | McBrayer et al. |
| 5,413,574 A | 5/1995 | Fugo |
| 5,514,130 A | 5/1996 | Baker |
| D377,524 S | 1/1997 | Lipp |
| 5,626,577 A | 5/1997 | Harris |
| 5,647,871 A | 7/1997 | Levine et al. |
| 5,683,385 A | 11/1997 | Kortenbach et al. |
| 5,709,224 A * | 1/1998 | Behl .................. A61B 18/1492 128/898 |
| 5,755,753 A | 5/1998 | Knowlton |
| 5,766,171 A | 6/1998 | Silvestrini |
| 5,868,744 A * | 2/1999 | Willmen ................ A61B 18/14 606/50 |
| 5,876,400 A | 3/1999 | Songer |
| 5,995,875 A | 11/1999 | Blewett et al. |
| 6,071,280 A | 6/2000 | Edwards et al. |
| 6,117,109 A | 9/2000 | Eggers et al. |
| 6,156,035 A | 12/2000 | Songer |
| 6,193,718 B1 | 2/2001 | Kortenbach et al. |
| 6,216,034 B1 * | 4/2001 | Hofmann ............... A61N 1/325 604/106 |
| 6,277,116 B1 | 8/2001 | Utely et al. |
| 6,309,387 B1 | 10/2001 | Eggers et al. |
| 6,346,078 B1 | 2/2002 | Ellman et al. |
| 6,395,001 B1 | 5/2002 | Ellman et al. |
| 6,432,105 B1 | 8/2002 | Ellman et al. |
| 6,562,032 B1 | 5/2003 | Ellman et al. |
| 6,610,060 B2 | 8/2003 | Mulier et al. |
| 6,620,156 B1 | 9/2003 | Garito et al. |
| 6,632,193 B1 | 10/2003 | Davison et al. |
| 6,638,275 B1 | 10/2003 | McGaffigan et al. |
| 6,746,447 B2 | 6/2004 | Davison et al. |
| 6,749,609 B1 | 6/2004 | Lunsford et al. |
| 6,772,012 B2 | 8/2004 | Ricart et al. |
| 6,773,431 B2 | 8/2004 | Eggers et al. |
| 6,837,884 B2 | 1/2005 | Woloszko |
| 6,896,672 B1 | 5/2005 | Eggers et al. |
| 6,920,883 B2 | 7/2005 | Bessette et al. |
| 6,921,398 B2 | 7/2005 | Carmel et al. |
| 7,150,747 B1 * | 12/2006 | McDonald ............ A61B 18/148 606/180 |
| 7,198,625 B1 | 4/2007 | Hui et al. |
| 7,270,658 B2 | 9/2007 | Woloszko et al. |
| 7,344,536 B1 | 3/2008 | Lunsford et al. |
| 7,357,798 B2 | 4/2008 | Sharps et al. |
| 7,384,417 B2 | 6/2008 | Cucin |
| 7,445,619 B2 | 11/2008 | Auge, II et al. |
| 7,500,974 B2 | 3/2009 | Sartor |
| 7,867,225 B2 | 1/2011 | Heim et al. |
| 7,867,226 B2 | 1/2011 | Heim et al. |
| 7,892,230 B2 | 2/2011 | Woloszko |
| 7,896,875 B2 | 3/2011 | Heim et al. |
| 7,935,109 B2 | 5/2011 | Cosmescu |
| 7,935,110 B1 | 5/2011 | Garito et al. |
| 7,935,111 B2 | 5/2011 | MacDonald |
| 7,935,112 B2 | 5/2011 | Heim et al. |
| 7,935,113 B2 | 5/2011 | Heim et al. |
| 8,007,493 B2 | 8/2011 | McGill et al. |
| 8,083,738 B2 | 12/2011 | Mirizzi et al. |
| 8,100,902 B2 | 1/2012 | Sartor |
| 8,103,355 B2 | 1/2012 | Mulholland |
| 8,133,223 B2 | 3/2012 | Docimo |
| 8,357,154 B2 | 1/2013 | Heim et al. |
| 8,357,155 B2 | 1/2013 | Heim et al. |
| 8,430,920 B2 | 4/2013 | Li et al. |
| 2001/0037107 A1 | 11/2001 | Zappala |
| 2002/0022870 A1 * | 2/2002 | Truckai ............... A61B 18/1485 607/101 |
| 2003/0088243 A1 | 5/2003 | Carmel et al. |
| 2003/0212396 A1 | 11/2003 | Eggers et al. |
| 2004/0181214 A1 * | 9/2004 | Garabedian ........ A61B 18/1477 606/41 |
| 2005/0222565 A1 | 10/2005 | Manstein |
| 2005/0245923 A1 | 11/2005 | Christopherson et al. |
| 2006/0276783 A1 | 12/2006 | Cosmescu |
| 2006/0293655 A1 | 12/2006 | Sartor |
| 2008/0071255 A1 | 3/2008 | Barthe et al. |
| 2008/0319442 A1 * | 12/2008 | Unger ................ A61B 18/1445 606/48 |
| 2009/0062792 A1 * | 3/2009 | Vakharia ............ A61B 18/1492 606/45 |
| 2009/0124958 A1 * | 5/2009 | Li ........................ A61B 18/203 604/20 |
| 2009/0138012 A1 | 5/2009 | Sartor |
| 2009/0192507 A1 | 7/2009 | Luttich |
| 2009/0275928 A1 | 11/2009 | Solomon et al. |
| 2010/0249772 A1 | 9/2010 | Mehta et al. |
| 2011/0054466 A1 * | 3/2011 | Rothstein ............ A61B 18/1477 606/41 |
| 2012/0029498 A1 | 2/2012 | Branovan |
| 2012/0123412 A1 | 5/2012 | Sartor |
| 2012/0149990 A1 | 6/2012 | Buehler et al. |
| 2012/0271294 A1 | 10/2012 | Barthe et al. |

\* cited by examiner

PERCUTANEOUS BLEPHAROPLASTY DEVICE AND METHOD

CROSS REFERENCE

This application claims domestic priority to U.S. Provisional Patent Application No. 61/847,218 filed Jul. 17, 2013, the contents of which are incorporated by reference in their entirety.

FIELD OF THE INVENTION

The invention generally relates to medical devices and associated methods of manufacture and use, and more particularly to electrosurgical devices and associated methods of manufacture and use.

BACKGROUND

Blepharoplasty is the plastic surgery operation for correcting defects, deformities and/or disfigurations of the eyelids. Excess deposits of eyelid fat can result in the appearance of puffiness around the eyes. The removal of this excess fat improves the overall look of the eyes, resulting in a more youthful and rested appearance of the individual.

Typically this procedure is done using one of two methods. The eyelid may be retracted to expose the underlying fat, which may then be removed using a number of different techniques. Alternatively, an incision may be made horizontally across the length of the eyelid to expose the fat pads underneath. Both of these methods utilize an incision and local anesthesia, and the incision may result in a scar.

SUMMARY

In a first aspect of the invention, there is a device, comprising a handle, two small parallel needle tips and an attachment means to an electrosurgical generator unit. The device is adapted to utilize bipolar electrosurgery with one of the needles serving as the active electrode and the other needle representing the return electrode. The device is adapted such that the electrosurgical current travels through the active electrode, passes through the tissue between the needle tips and run into the return electrode. During this process, the tissue shrinks and/or retracts as a result of the electrosurgical current.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The invention generally relates to medical devices and associated methods of manufacture and use, and more particularly to electrosurgical devices and associated methods of manufacture and use. In accordance with aspects of the invention, there is an electrosurgical device that is configured for performing a percutaneous blepharoplasty procedure. In surgery, and as used herein, the term "percutaneous" pertains to a medical procedure where access to inner organs or other tissue is done via needle-puncture of the skin, rather than by using an open approach where inner organs or tissue are exposed via an incision (e.g., a scalpel incision). Implementations of the invention allow for a blepharoplasty procedure to be done percutaneously, without the use of anesthesia or requiring any incisions. Using a percutaneous blepharoplasty procedure according to aspects of the invention advantageously results in reduced procedural time and minimizes or eliminates bleeding and scarring relative to other types of blepharoplasty procedure that involve incisions.

In embodiments, an electrosurgical device includes a handle, two small parallel needle tips, and an attachment means to an electrosurgical generator unit. The device may utilize bipolar electrosurgery with one of the needles serving as the active electrode and the other needle representing the return electrode. In embodiments, the electrosurgical current travels through the active electrode, passes through the fat tissue between the needle tips, and runs into the return electrode. During this process, the fat tissue between the needle tips may shrink and retract due to the application of the electrosurgical current via the needle tips.

As used herein, a "bovie" can refer an instrument used for electrosurgical procedures, such as dissection, ablation, and hemostasis. The term "bovie" may also be used as a verb/action, and is frequently used as a synonym for electrocautery (e.g., to bovie a blood vessel). The term "bovie" may also refer to the electrosurgical current that is being applied (e.g., to apply the bovie to the tissue).

In embodiments, an electrosurgical device includes a hand held surgical instrument having a pencil grip type hand-piece. A tip from which the needles extend is connected to the hand-piece and may be angled to improve visualization of the user holding the device. The hand-piece may be selectively separable from the tip, such that a single hand-piece may be reusable with different disposable tips. Alternatively, the hand-piece, tip, and attachment means may be integrally connected as a unit. In either configuration, the tip may be structured and arranged to be selectively rotatable relative to the hand-piece in order to adjust the needle entry into the skin.

The attachment means may include a standard cord that has an appropriate connection to attach to a standard electrosurgical generator unit. Actuation of the electrosurgical current via the needles may be controlled using a foot pedal that is operatively connected to the electrosurgical generator unit. Alternatively, actuation of the electrosurgical current via the needles may be controlled using a button on the hand-piece.

In aspects described herein, the tip may include two needles that are configured to puncture the skin and also serve as electrodes for conveying the electrosurgical current to tissue under the skin. The needles may be very small needles, e.g., on the order of approximately 27-30 gauge, which equals a diameter of about 0.012" to 0.016". The needles may have a length of about 0.25" to 0.5", and preferably about 1.5 cm. The needles may be insulated on their exterior surfaces except near their respective needle tips (i.e., distal ends) so a current can pass across the needle tips. The insulation may be configured to protect the surrounding tissues during use.

The needles and/or the tip that houses the needles may have a number of additional features. In one aspect, the needles are structured to be movable relative to each other, either translating in a parallel fashion towards or away from each other or actuating in a scissoring fashion towards or away from each other. The relative movement between the needles may be provided and controlled by an actuator that is on the hand-piece. In another aspect, the needles may extend and/or retract from the hand-piece via an actuator on the hand-piece. In additional aspects, the needles may be cooled to help prevent additional damage to surrounding tissues. The cooling may be provided by a heat transfer device in the hand-piece (e.g., a heat sink, forced air cooling device, liquid cooling system, etc.) that is configured to transfer heat away from the needles in order to lower the temperature of the needles. In further aspects, the tip may be configured to oscillate from side to side to increase the coverage during use. In still further aspects, the needles or a second set of needle(s) may provide electrical stimulation to the surrounding muscles to aid in the tightening of the muscles following fat removal.

In accordance with aspects of the invention, a method of using the electrosurgical device includes the following steps. The needles are inserted under the skin in an angled manner directed lateral to medial. The needles are inserted down through the skin and muscle, to the fascial/fat layer. Once appropriate depth is achieved, the bovie (e.g., the electrosurgical current) is applied to the fat. The needles can be slowly withdrawn laterally through a fat section, e.g., along the fascia ridge. If applicable, the needles may oscillate, move apart or be cooled. The needles are then withdrawn from the skin, and moved over laterally to the next section. The previous steps are repeated across the width of the section to be treated.

In accordance with additional aspects of the invention, the electrosurgical device may have only a single needle (rather than two needles) having first and second electrode sections. For example, the single needle may be covered with an electrical insulator, and two separate portions of the needle may be exposed (not covered by the insulator) to provide the respective electrode sections.

In accordance with additional aspects of the invention, the device may include selectively extendable and/or retractable needle(s). For example, a cannula may be provided which houses one or more electrodes in a retracted position. An actuator (e.g., a push button or the like) may be provided to selectively extend the needle(s) out of the retracted position to an extended/exposed position. The needle(s) may be used to apply the electric charge in the manner described herein when in the extended/exposed position. The actuator, or a different actuator, may be used to move the needle(s) from the extended/exposed position back to the retracted position. The device may automatically move the needle(s) from the extended/exposed position back to the retracted position, e.g., by a spring or other mechanism, e.g., when the user releases the actuator. In this manner, the needle(s) are retracted for safety, appearance, etc., when not in use, and selectively extended when it is desired to apply the electric charge to the tissue.

Figure 1A:
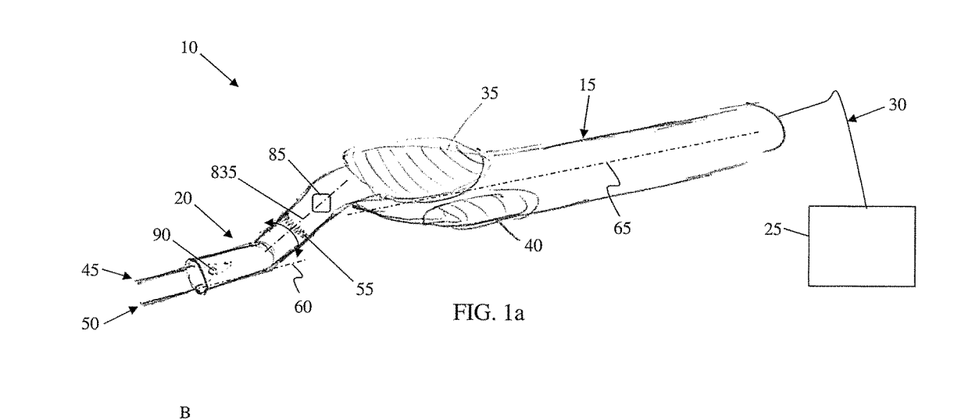
FIGS. 1a-1d and 2 show aspects of an electrosurgical device in accordance with aspects of the invention.

FIGS. 1a-1d, and 2 show aspects of an electrosurgical device in accordance with aspects of the invention. FIG. 1a shows an electrosurgical device 10 comprising a hand-piece 15 and a tip 20. The hand-piece 15 is operatively connected to an electrical energy source 25 via an attachment means 30. The electrical energy source 25 may be a conventional device that generates electrical current or potential for use in electrosurgical procedures, such as an electrosurgical current generator, an RF power supply, etc. The attachment means 30 may be a conventional device, such as an electrical cord that is selectively connectable to each of the hand-piece 15 and the electrical energy source 25 to convey the electrosurgical current from the electrical energy source 25 to the hand-piece 15. Alternatively, the attachment means 30 may be integrally connected to one or both of the hand-piece 15 and the electrosurgical current generator 25.

Figure 1B:
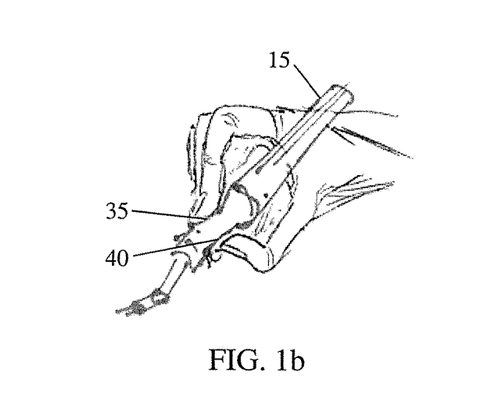

The hand-piece 15 shown in FIG. 1a may include ergonomic grip sections. Specifically, the hand-piece 15 may include an index finger grip 35 and/or a thumb grip 40. These grips may be ergonomically configured to facilitate a user holding the hand-piece 15 like a pencil as shown in FIG. 1b, which helps a user orient the tip 20 of the device 10 during a procedure.

With continued reference to FIG. 1a, the tip 20 is at a distal end of the hand-piece 15 and includes two needles 45, 50 each having a respective free end extending outward from the tip 20. The hand-piece 15 and the tip 20 may be provided with electrical conductive features (e.g., wires, contacts, etc.) that communicate the electrical current from the electrical energy source 25 to at least one of the needles 45, 50. The electrical conductive features may be arranged in a conventional fashion, e.g., using wires and/or contacts, etc. In this manner, the needles 45, 50 may be inserted into a tissue and serve as electrodes, such that the electrosurgical current from the electrical energy source 25 may be applied to the tissue between the two needles 45, 50 as would be readily understood by one of ordinary skill in the art such that further explanation is not necessary. In this manner, the device 10 may be used to perform an electrosurgical percutaneous blepharoplasty procedure by inserting the ends of the needles 45, 50 into the tissue (e.g., fat) via puncturing the skin, without requiring an incision in the skin.

Figure 1C:
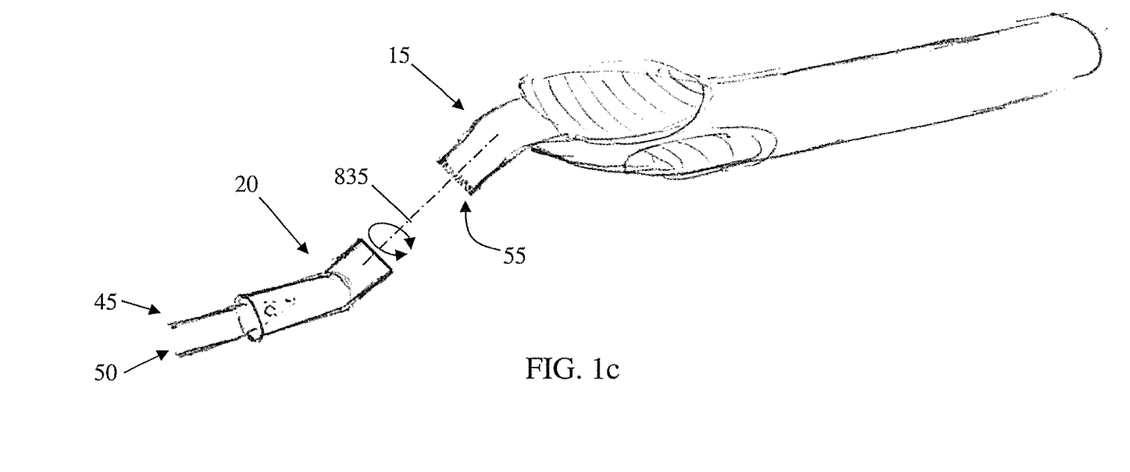

As illustrated in FIGS. 1a and 1c, the tip 20 may be selectively connected to and detached from the hand-piece 15. For example, the tip 20 may be selectively connected to the hand-piece 15 by a connector 55, such as a threaded connector, bayonet connector, detent fitting, friction fit, or the like. In embodiments where the tip 20 is selectively connectable to and detachable from the hand-piece 15, the tip 20 and the hand-piece 15 may be provided with electrical contacts that come into contact to create a continuous conductive path from the hand-piece 15 to the needles 45, 50 when the tip 20 is connected to the hand-piece 15. The tip 20 and/or the hand-piece 15 may be provided with structural features, such as guides, etc., that urge the tip 20 to be connected to the hand-piece 15 in a position/orientation relative to the hand-piece 15 that completes the electrical connection between the electrical contacts. In this manner, the tip 20 including the needles 45, 50 may be a disposable part that is replaced, e.g., for each procedure, while the same hand-piece 15 and the electrical energy source 25 may be used many times over in plural different procedures.

Figure 1D:
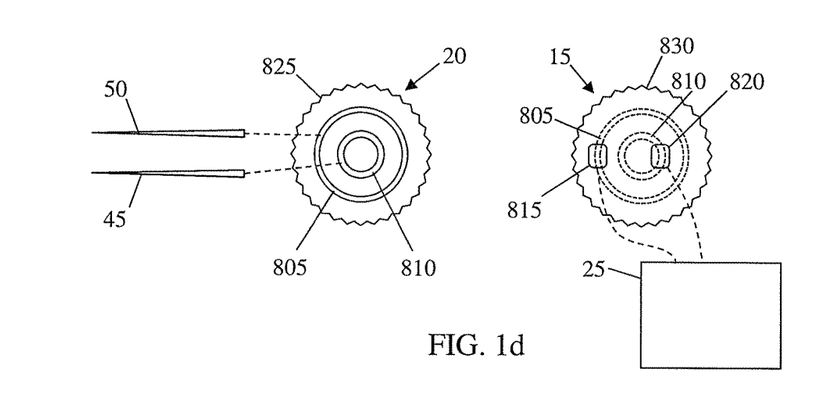

With continued reference to FIGS. 1a and 1c, in a preferred embodiment the connector 55 permits the tip 20 to rotate relative to the hand-piece 15 about an axis 835 while the tip 20 is connected to the hand-piece 15. FIG. 1d shows details of an exemplary connection between the tip 20 and the hand-piece 15 in accordance with aspects of the invention that facilitates such rotation. FIG. 1d shows a diagrammatic end view of the tip 20 and a diagrammatic end view of the hand-piece 15 in accordance with this embodiment. The tip 20 includes substantially circular electrical contacts 805 and 825, that are respectively electrically connected to needles 45, 50 (e.g., via wiring and/or other contacts in the tip 20) as indicated by the dashed lines. The hand-piece 15 includes pad or brush style contacts 815 and 820 that are respectively electrically connected to the electric energy source 25 (e.g., via wiring and/or other contacts in the hand-piece 15) as indicated by the dashed lines. The tip 20 and the hand-piece 15 and sized and shaped such that when the tip 20 is connected to the hand-piece, contact 815 touches circular contact 805, and contact 820 touches circular contact 810 (as represented by dashed lines). Due to the circular shape of the contacts 805 and 810, this arrangement maintains electrical continuity from the source 25 to the needles 45, 50 even when the tip 20 is rotated relative to the hand-piece 15. The invention is not limited to this particular electrical contact arrangement, and any suitable arrangement may be used.

Still referring to FIG. 1d, rotation of the tip 20 relative to the hand-piece 15 (e.g., about axis 835 as shown in FIGS. 1a and 1c) may be controlled by engagement elements. For example, the tip 20 may include at least one detent or engagement element 825, and the hand-piece 15 may include at least one detent or engagement element 830 that corresponds in size and shape to that of element 825. When the tip 20 is connected to the hand-piece 15 (e.g., as shown in FIG. 1a), the elements 825 and 830 may be engaged such that friction between the elements 825, 830 inhibits rotation of the tip 20 relative to the hand-15. When a sufficient force is applied to overcome the friction between the elements 825, 830, the tip 20 may rotate relative to the hand-piece 15. In this manner, the elements 825, 830 may provide predefined rotational positions that the tip 20 can click into relative to the hand-piece 15. This rotation facilitates the user maneuvering their hand and body around a patient while holding the device 10 and keeping the needles in a desired position relative to the patient.

With continued reference to FIG. 1a, the hand-piece 15 and/or the tip 20 may be shaped such that a longitudinal axis 60 of at least one the needles 45, 50 is offset from a longitudinal axis 65 of the hand-piece 15. For example, the axis 60 may be offset from and parallel to axis 65 as shown in FIG. 1a. The axis 60 may be coaxial with one of the needles 45, 50, or may be an axis that is between and parallel to the longitudinal extent of both needles 45, 50. This angled shape makes it easier for the user holding the device 10 to see the tips of the needles 45, 50 during a procedure. In another example shown in FIGS. 5a-b, the needles 45', 50' may be shaped (e.g., bent) such that the distal ends of the needles are angled relative to the longitudinal axis of the hand-piece 15'.

Figure 2:
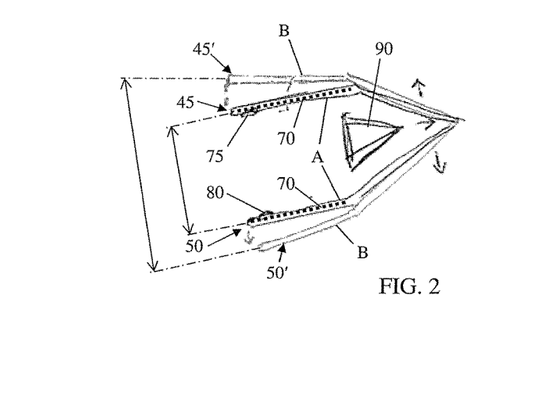

The needles 45, 50 may have any suitable size. In an exemplary implementation, the needles 45, 50 have a size on the order of approximately 27-30 gauge, or a diameter of about 0.012" to 0.016". The needles may have a length of about 0.25" to 0.5", and preferably about 1.5 cm. The needles 45, 50 may be electrically insulated on their exterior surfaces except near their respective needle tips (i.e., distal ends) so a current can pass across the needle tips. The insulation 70 may be configured to protect the surrounding tissues during use. As shown in FIG. 2, in one embodiment, the electrical insulation covers substantially the entirety of the portions of the needles 45, 50 that extend outward form the tip 20 except for respective areas 75, 80 near the needle tips. The electrical insulation 70 may comprise, for example, a plastic coating on the exterior surface of the needles. In additional aspects, the needles 45, 50 may be cooled to minimize the risk of heat-induced damage to surrounding tissues due to electrical resistive heating. The cooling may be provided by a heat transfer device 85 (e.g., a heat sink, forced air cooling device, liquid cooling system, etc.) in the hand-piece 15 and/or the tip 20, wherein the heat transfer device 85 is in direct or indirect contact with the needles 45, 50 and is configured to transfer heat away from the needles 45, 50 in order to lower the temperature of the needles 45, 50.

According to aspects of the invention, the tip 20 and needles 45, 50 may be configured to provide a user-controlled amount of relative movement between the needles 45, 50 in order to change the treatment area of the device 10. For example, as shown in FIG. 2, the needles 45, 50 may be selectively moveable between a first position "A" and a second position "B". The positions may be configured such that the tips of the needles are spaced apart from one another more in the second position than in the first position. Additionally or alternatively, the positions may be configured such that the needles are at different angles relative to one another if the first position (e.g., parallel) and the second position (e.g., acute angle). This needle separation variability provides the advantages of: a differential treatment zone; different amounts of electrical energy delivered to the tissue due to different separation; and a broader area to hold back fat tissue.

In embodiments, the tip 20 and/or the hand-piece 15 is provided with an actuating mechanism that selectively moves the needles 45, 50 between the first position and the second position. In one example, the actuating mechanism comprises a wedge 90 that moves relative to and against the needles 45, 50 when the user squeezes the grips 35, 40 between their finger and thumb. A motion produced by the squeezing action of the grips 35, 40 may be conveyed to the wedge 90 by one or more suitable elements, which may include but are not limited to any one or more of cams, levers, inclined surfaces, gears, etc. When the user releases the squeezing force, the wedge 90 may be resiliently urged back to its initial position, such that the needles 45, 50 automatically return to the first position.

Figure 3:
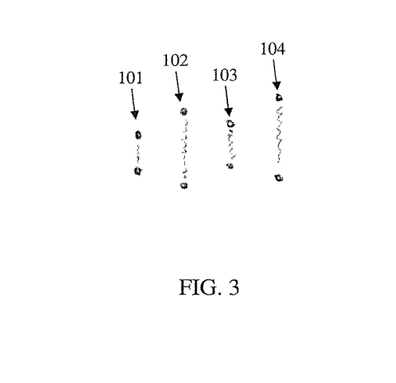
FIGS. 3 and 4a-4d show aspects of a method of using an electrosurgical device in accordance with aspects of the invention.

FIG. 3 shows a diagram of treatment sites in accordance with aspects of the invention. The black dots represent the needle tips at respective treatment sites 101-104. At sites 101 and 103, the needles 45, 50 are in the first position (e.g., relatively narrow position A of FIG. 2) when they pierce the skin. At sites 102 and 104, the needles 45, 50 are in the second position (e.g., relatively wide position B of FIG. 2) when they pierce the skin, e.g., via the actuating mechanism. In this exemplary method of use, the user applies the squeezing force (actuates the actuating mechanism) when moving from site 101 to site 102 to widen the needles before piercing the skin at site 102. Then after the treatment at site 102, the user releases the squeezing force, such that the needles automatically return to the narrower arrangement prior to piercing the skin at site 103. In this manner, the user may temporarily change the treatment zone on the fly during a procedure.

In a particular embodiment, the needles 45, 50 are biased to a first position in which the needles are relatively far apart from one another, and the user may apply an actuating force (e.g., to an actuating mechanism such as that shown in FIGS. 1a and 2 or FIGS. 7a-d) to move the needles to a second position in which the needles are move closer to one another. The first position may be configured based on the electrical energy supplied by the source 25 such that an amount of electrical energy sufficient to affect the tissue (e.g., burn, ablate, shrink the tissue) will not transfer from the first needle to the second needle when the needles are in the first position. For example, an amount of electrical energy sufficient to affect the target tissue (e.g., burn, ablate, shrink the tissue) will not transfer because it cannot overcome the resistance of the material (e.g., air, tissue) extending between the needles. As the user applies the actuating force to move the needles closer together, the distance between the needles reaches a point where an amount of electrical energy sufficient to affect the tissue does transfer from the first needle to the second needle. At this point the user can see and or hear the effect of the electrical energy on the tissue (e.g., the tissue contracts, burns, etc.). The user thus has a way to control the application of the electrical energy to the tissue based on applying the actuating force that moves the needles closer to one another. The tip 20 may be configured such that when the user releases the actuating force, the needles automatically move apart from one another back toward the first position. Any suitable actuating mechanism may be used to achieve this relative movement of the needles. The actuating mechanisms described with respect to FIGS. 1a, 2, and 7a-d are merely exemplary and are not intended to limit the invention.

Figure 4A:
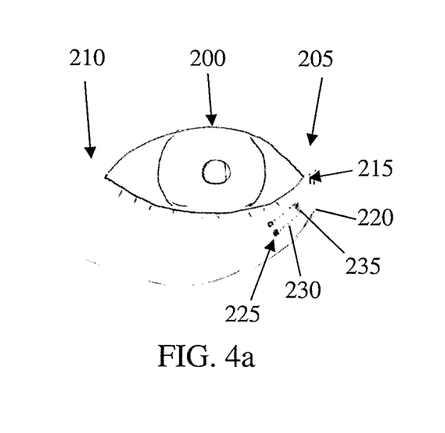
Figure 4B:
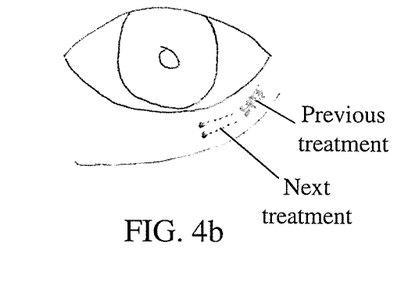
Figure 4C:
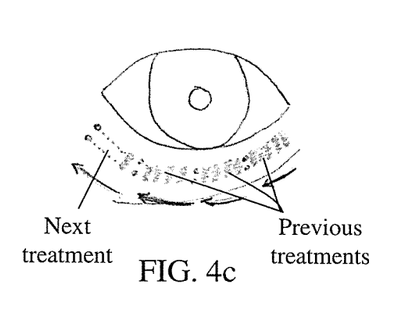
Figure 4D:
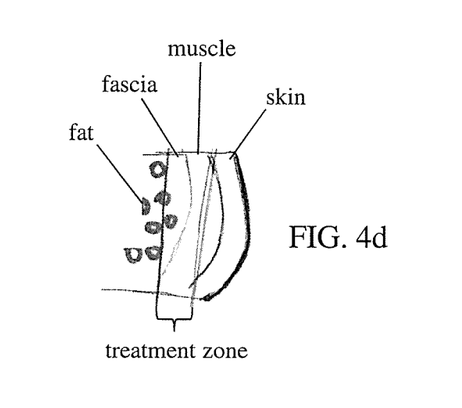

FIGS. 4a-4d illustrate a method of treatment using the electrosurgical device in accordance with aspects of the invention. As depicted in FIG. 4a, a patient eye 200 has a medial side 205 and a lateral side 210. Also depicted are the lid 215 and the rim of the orbit 220. Sites 225 represent where the needles 45, 50 pierce the skin. Dotted lines 230 represent the needles 45, 50 passing from sites 225 through and under the skin into tissue such as muscle, fascia, and fat. Shaded area 235 represents the treatment zone where electrical energy is applied to the tissue via the needles 45, 50. In embodiments, both needles are inserted under the skin to their hubs, e.g., to the treatment depth, starting medially (i.e., pushing the needles into the tissue toward the medial side). In embodiments, the treatment depth is the muscle to fascia and fat layer. In a particular embodiment, the device 10 is controlled such that the electrical energy is not applied via the needles 45, 50 while the needles 45, 50 are being inserted into the tissue; then, after reaching the treatment depth, the electrical energy (e.g., the electrosurgical current from the electrical energy source 25) is applied to the tissue via the needles 45, 50 while the needles 45, 50 are being pulled out of the tissue. These steps are repeated as shown in FIGS. 4b and 4c, with the direction of successive treatments being from the medial side 205 toward the lateral side 210 as shown by the arrows in FIG. 4c. FIG. 4d shows a preferred treatment zone at an eyelid cross section.

FIGS. 5a-5b, 6a-6b, and 7a-7d show aspects of electrosurgical devices 10', 10", 10''' in accordance with aspects of the invention. The electrosurgical devices 10', 10", 10''' may include any one or more of the features of electrosurgical device 10 (e.g., as described in FIGS. 1a-c and/or FIG. 2). For example, similar to device 10, each of the devices 10', 10", 10''' is configured to be connected to an electrosurgical current generator for the purpose of applying electrical energy to tissue via that needles acting as electrodes.

Figure 5A:
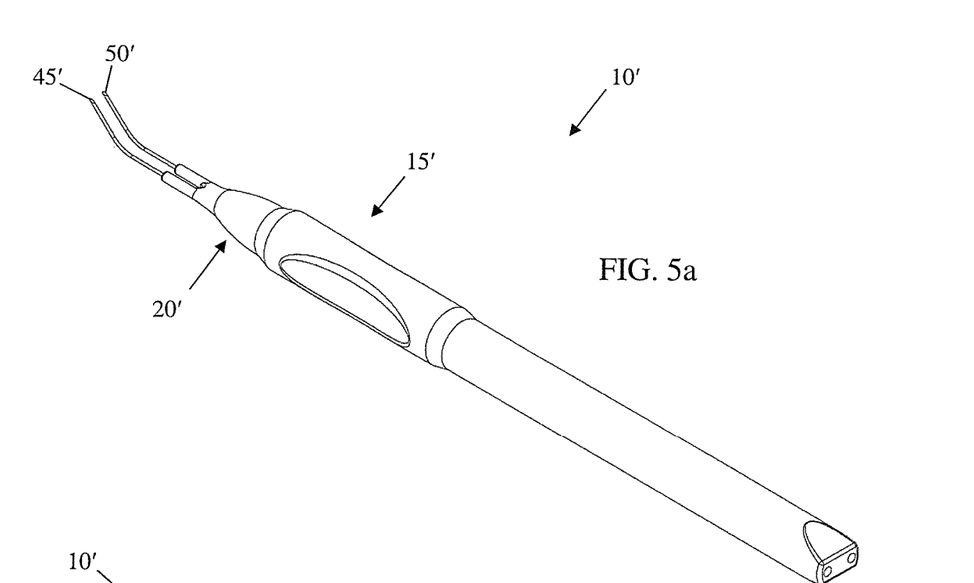
FIGS. 5a-5b, 6a-6b, and 7a-7d show aspects of electrosurgical devices in accordance with aspects of the invention.
Figure 5B:
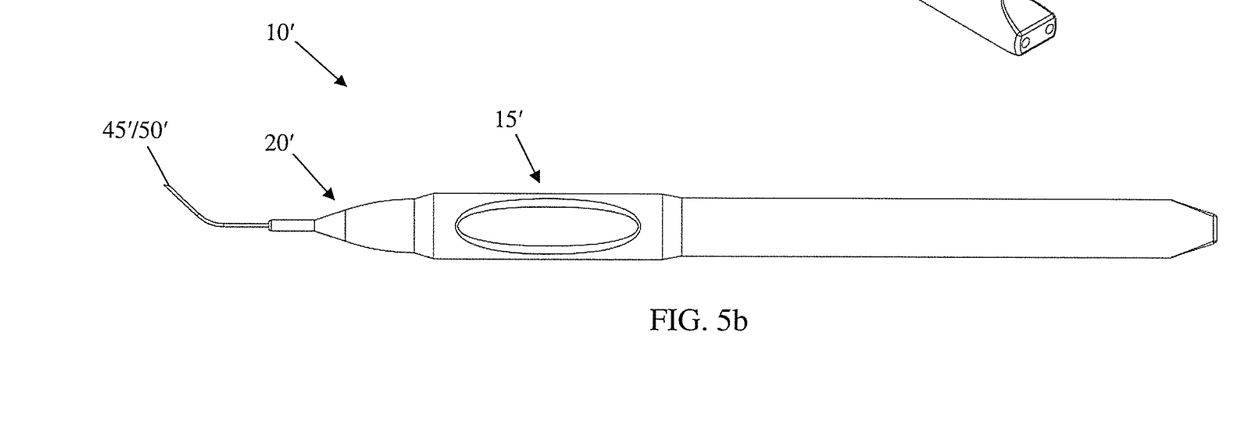

FIGS. 5a-5b show another embodiment of electrosurgical device 10' comprising a hand-piece 15', tip 20', and needles 45' and 50'.

Figure 6A:
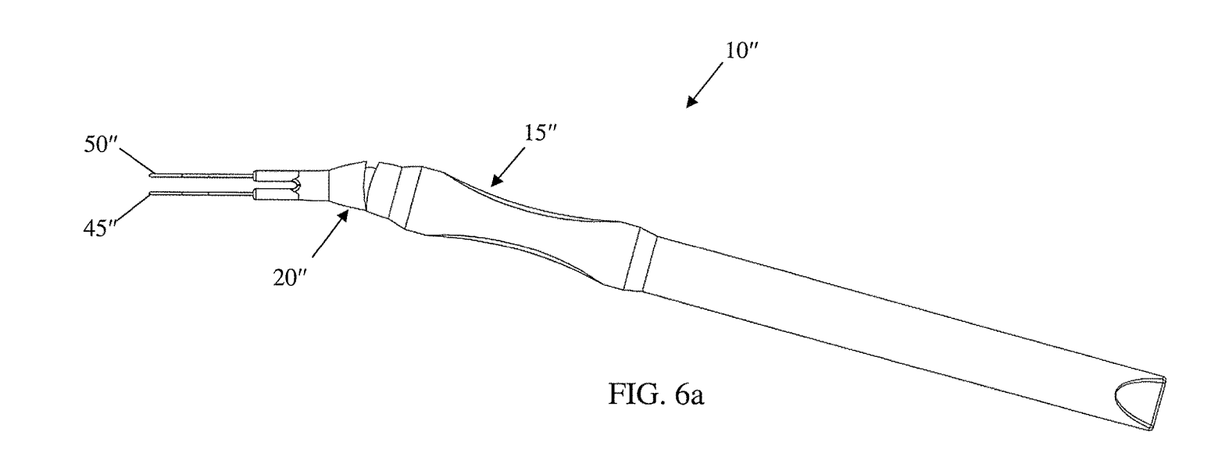
Figure 6B:
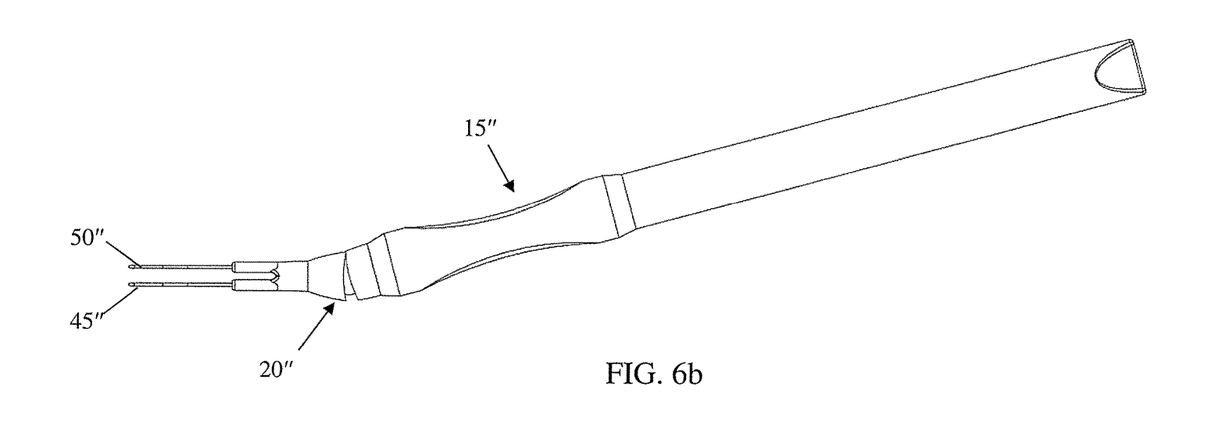

FIGS. 6a-6b show another embodiment of electrosurgical device 10" comprising a hand-piece 15", tip 20", and needles 45" and 50". In this embodiment, the tip 20" may pivot relative to the hand-piece 15". The pivoting may be provided by a mechanism in the tip 20" that permits the movement while maintaining the electrical continuity between the wiring in the hand-piece 15" and the needles 45" and 50".

Figure 7A:
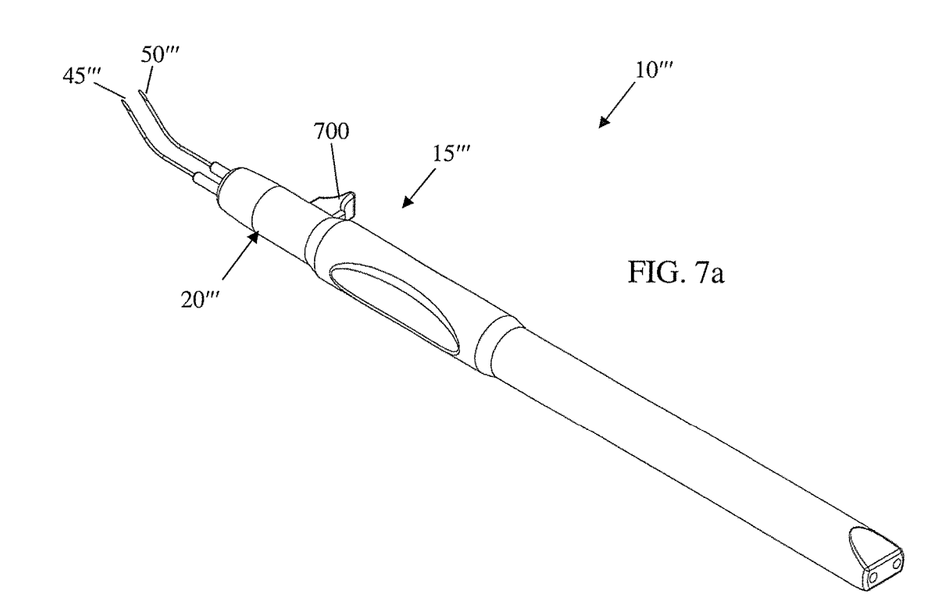
Figure 7B:
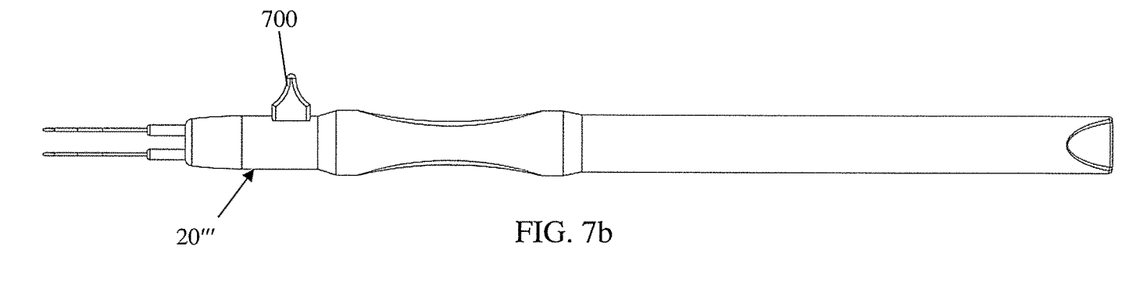
Figure 7C:
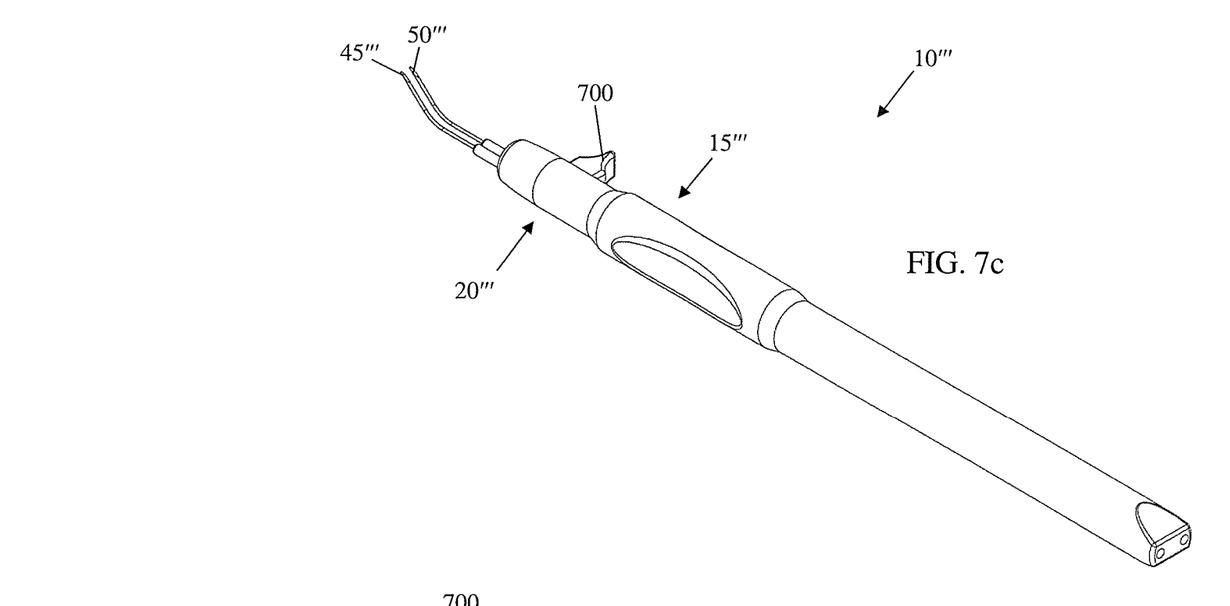
Figure 7D:
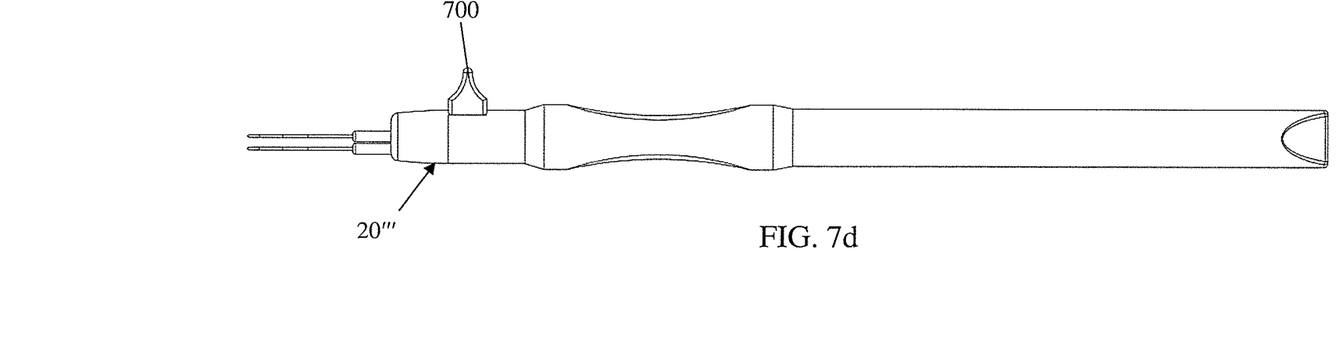

FIGS. 7a-7d show another embodiment of electrosurgical device 10''' comprising a hand-piece 15''', tip 20''', and needles 45''' and 50'''. In this embodiment, the tip 20''' includes an actuator 700 that causes the needles 40''' and 50''' to move between a first position (FIGS. 7a and 7b) and a second position (FIGS. 7c and 7d). The actuator 700 may comprise an actuating mechanism that includes a slide element that is directly or indirectly linked to the needles 45''' and 50''', whereby sliding the slide element transmits a force to the needles that causes the needles to move away from each other or toward one another. In FIG. 7b the actuator 700 has been manually moved to a first position on the tip, and in FIG. 7d the actuator 700 has been manually moved to a second position on the tip. The spacing between the needles 45''' and 50''' in the first position (FIGS. 7a and 7b) may be about 5 mm, and the spacing between the needles 45''' and 50''' in the second position (FIGS. 7c and 7d) may be about 2 mm.

Embodiments of the invention include an electrosurgical device as described herein. Further embodiments of the invention include a method of manufacturing an electrosurgical device as described herein. Even further embodiments of the invention include a method of performing percutaneous blepharoplasty using an electrosurgical device as described herein.

In accordance with an aspect of the invention, an electrosurgical device as described herein may comprise a hand-held surgical instrument for use in blepharoplasty procedures, wherein the instrument includes: a handle having a long axis; a means by which the handle may be connected to an electrosurgical generator (or RF power supply); and a set of needles partially retained in said handle, and partially extended from one end of the handle. The needles are sized in the 20-30 gauge range, and beveled at the tip to minimize resistance as the tissue is penetrated. The needles taking on a non-linear pathway in the extended region such that they create an obtuse angle with the long axis of the hand-piece. The needles may be insulated along their length, to protect the skin layer through which the needle passes, with a 3-5 mm exposed portion at the distal tip of the needles. The spacing distance between said needles may be adjustable over a range of 2-5 mm. The spacing distance being controlled by an actuation means within the handle. The distal tip of the handle may be pivotable or rotatable such that the orientation of the needles can be adjusted relative to the long axis of the handle.

In accordance with an aspect of the invention, there is a method for aesthetically modifying the eyelid by removal of excess fat tissue using an electrosurgical device as described herein. The method comprises: inserting the needles under the skin in an angled manner directed lateral to medial; the needles are inserted down through the skin and muscle to the fascial/fat layer; once the fat tissue is approximated a current is applied to the needles; the separation distance of the needles is appropriately adjusted to optimize fat removal; with continual current applied, the needles are withdrawn laterally through the fat section; and, once the fat section has been traversed, the current is stopped and the needles are withdrawn.

In accordance with aspects of the invention, there is a percutaneous blepharoplasty electrosurgical device comprising: a hand-piece; a tip connected to the hand-piece; and two needles extending from a distal end of the tip. The hand-piece is structured and arranged to connect to an electrical energy source, and to convey electrical energy from the electrical energy source to the needles in a percutaneous blepharoplasty procedure. In some embodiments, the tip is selectively connectable to and detachable from the hand-piece. In some embodiments, the tip is selectively relative to the hand-piece when the tip is connected to the hand-piece, while electrical continuity is maintained between the tip and the hand piece (see, e.g., FIG. 1d). In some embodiments, the device includes an actuating mechanism for selectively moving one or both of the needles to increase and/or decrease the spacing between the needles while the tip is connected to the hand-piece. In a preferred embodiment, the actuating mechanism biases the needles to a first position and permits the user to move the needles closer to one another (e.g., closer than in the first position) by applying an actuating force. In a particularly preferred embodiment, a sufficiently low power electric source is used and the tip and the needles are structured and arranged such that electrical energy from the source does not transfer from the first needle to the second needle when the needles are in the first position, and does transfer the electrical energy from the first needle to the second needle at some point while the needles are moved closer together due to the user applying an actuating force to the mechanism. A method of using the particularly preferred embodiment includes: sticking the needles through the skin and into the target tissue while the needles are in the first (wide spaced apart) position, such that electrical energy sufficient to affect (e.g., burn, ablate, shrink) the tissue does not transfer from one needle to the other since the needles are too far apart to support such transfer; applying an actuating force to the actuating mechanism to move the needles closer together until such time as the needles are sufficiently close to one another to permit an amount of electrical energy sufficient to affect the tissue (e.g., burn, ablate, shrink the tissue) to transfer from the first needle to the second needle; and one of releasing the actuating force before removing the needles from the tissue, or releasing the actuating force while removing the needles from the tissue, or releasing the actuating force after removing the needles from the tissue.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:
1. A device, comprising:
a hand-piece;
a tip at a distal end of the hand-piece; and
two needles each having a respective free end extending outward from the tip;
wherein the hand-piece is selectively connectable to an electrical energy source by an attachment that is configured to convey electrosurgical current from the electrical energy source to the hand-piece;
the hand-piece is configured to convey the electrosurgical current to at least one of the needles;
the device is adapted to utilize bipolar electrosurgery with one of the needles serving as the active electrode and another one of the needles representing the return electrode,
the device is adapted such that the electrosurgical current travels through the active electrode, passes through a tissue between the needles, and runs into the return electrode, such that the tissue shrinks and/or retracts as a result of the electrosurgical current;
the tip is rotatable relative to the hand-piece about an axis that is angled relative to a longitudinal axis of the hand-piece;
the hand-piece comprises a finger grip and a thumb grip;
the tip comprises a wedge configured to move relative to and against the needles;
the wedge is moveable to a first position that causes the needles to be parallel to one another, outside a housing of the tip, and spaced apart by a first distance; and
the wedge is moveable to a second position that causes the needles to be at an acute angle relative to one another, outside the housing of the tip, and spaced apart by a second distance different than the first distance.

2. A device, comprising:
a hand-piece;
a tip at a distal end of the hand-piece; and
two needles each having a respective free end extending outward from the tip;
wherein the hand-piece is selectively connectable to an electrical energy source by an attachment that is configured to convey electrosurgical current from the electrical energy source to the hand-piece;
the hand-piece is configured to convey the electrosurgical current to at least one of the needles;
the device is adapted to utilize bipolar electrosurgery with one of the needles serving as the active electrode and another one of the needles representing the return electrode,
the device is adapted such that the electrosurgical current travels through the active electrode, passes through a tissue between the needles, and runs into the return electrode, such that the tissue shrinks and/or retracts as a result of the electrosurgical current;
the tip is rotatable relative to the hand-piece about an axis that is angled relative to a longitudinal axis of the hand-piece;
the hand-piece comprises a finger grip and a thumb grip on opposite sides of a generally cylindrical housing;
the tip comprises a wedge configured to move relative to and against the needles;
the wedge is configured to move from the first position to the second position based on a squeezing force applied to the finger grip and the thumb grip; and
the wedge is configured to move from the second position to the first position based on the squeezing force being released.

* * * * *